United States Patent

Cohen

Patent Number: 5,078,603
Date of Patent: Jan. 7, 1992

[54] FILTERING SUCTION NOZZLE

[76] Inventor: Howard Cohen, 339 Forest Ave., Woodmere, N.Y. 11598

[21] Appl. No.: 410,914

[22] Filed: Sep. 22, 1989

[51] Int. Cl.$^5$ ............................................. A61C 17/00
[52] U.S. Cl. ......................................... 433/91; 433/96
[58] Field of Search .................. 433/91, 92, 96; 604/268, 190, 902, 42, 48; 15/420, 422; 222/189; 210/461; 137/140

[56] References Cited

U.S. PATENT DOCUMENTS

| | | | |
|---|---|---|---|
| 128,257 | 6/1872 | Snyder | 604/190 |
| 1,192,408 | 7/1916 | Frame | 15/422 |
| 3,890,712 | 6/1975 | Lopez | 433/92 |
| 4,051,981 | 10/1977 | Mandlak | 222/189 |
| 4,158,916 | 6/1979 | Adler | 433/91 |
| 4,265,621 | 5/1981 | McVey | 433/91 |
| 4,417,874 | 11/1983 | Andersson et al. | 433/96 |
| 4,587,687 | 5/1986 | Ikonen et al. | 15/422 |

FOREIGN PATENT DOCUMENTS 3316397  1/1985  Fed. Rep. of Germany ........ 433/92

Primary Examiner—Cary E. O'Conner
Attorney, Agent, or Firm—Robert W. Fiddler

[57] ABSTRACT

A filtering suction nozzle particularly adapted for use in connection with a dental or medical suction system. The nozzle is suited for use as a high speed suction tip and/or a saliva ejector formed of an elongate tube defining a fluid flow path therethrough. Filtering means are arranged within the tube in the flow path of any fluid passing therethrough, and coupling means are arranged at one end of the tube to connect the tube to a suction line from a suction source. The tube may be formed with flexible pleats to facilitate bending. According to the method of the invention, filtering means are arranged in the flow path of any existing suction nozzles to thereby reduce debris collection in the suction system and minimize possible patient infection from previously collected debris.

8 Claims, 1 Drawing Sheet

FILTERING SUCTION NOZZLE

This invention relates to the art of fluid suction systems, and more particularly to an improved suction nozzle for use in a dental or medical suction system to minimize the need for periodic trap cleaning and flushing of the suction system, and reduce the possibility of patient infection by previously collected debris.

BACKGROUND OF THE INVENTION

Conventional suction systems such as employed in the dental and medical fields generally employ a central suction system from which suction conduits, usually in the form of flexible hoses or tubes, are extended. Replaceable suction nozzles are removably secured at the end of the hoses or tubes to pick up a variety of medical debris such as is developed during dental or surgical procedures. Such suction systems are generally provided with some sort of central filter or trap arranged in the suction system to separate the collected debris from the fluid stream. These filtering arrangements must be periodically cleaned, requiring messy and rather involved procedures for removing the filter traps and flushing of the system. Aside from the unpleasantness of the cleaning job, leakage problems often arise in removing and replacing the filters and traps.

So as to minimize the handling problem, disposable filters have been evolved. However, even these entail rather involved manipulations and handling for removal.

Further, even with periodic cleaning of the trap and disposal of the filters, in normal procedures, the filters are rarely cleaned more than once each day, and a large number of patients are treated with the same suction equipment, so that there is a possibility of patient contamination by materials which have been filtered from previous patients.

Additionally, previously employed nozzles when bent to fit over the lips of a patient require holding wires, and result in a diminution of nozzle cross-section at the bend.

BRIEF SUMMARY OF THE INVENTION

It is with the above considerations in mind that the present improved suction nozzle has been evolved, minimizing the likelihood of contamination of one patient by the debris collected from a previous patient, and permitting bending to a desired contour without diminution of flow.

It is accordingly among the primary objects of this invention to provide an improved suction nozzle for use in a dental or medical suction system which will minimize the possibility of contaminating a subsequently treated patient with the debris collected from a previous patient.

Another object of the invention is to reduce the cleaning requirements of suction systems employed in dental and medical procedures.

A further object of the invention is to provide a nozzle which can readily be bent to a desired contour.

These and other objects of the invention are achieved by providing a nozzle formed of relatively inexpensive material such that the entire nozzle may be economically disposed of after each use. The disposable nozzle is formed of an elongate fluid conducting tube. Filter means are arranged within the tube in the flow path of any fluid passing therethrough with the filter means serving to retain and separate from the fluid any debris. The nozzle is formed with appropriate coupling means at one end thereof for securement to a suction system. To facilitate bending to a desired contour, the nozzle may be formed with transversely extending accordion folds along at least a portion of the length thereof, at least at the points where bending is desired.

A feature of the invention resides in the fact that by collecting the debris in the nozzle, the possibility of back-up from a central trap in the central system is minimized.

Another feature of the invention resides in the fact that after use, the nozzle along with any debris separated by the filter therein may readily be discarded in a safe, sanitary fashion, minimizing collections of debris at a central point in the suction system.

A futher feature resides in the use of transversely extending accordion folds along at least a portion of the length of a nozzle to facilitate bending of the nozzle to the desired shape, and also permitting selective length selection, and bending without reducing interior cross-section.

BRIEF DESCRIPTION OF THE DRAWINGS

The specific details of the best mode contemplated by applicant for carrying out the invention, and of the manner and process of making and using it so as to enable those skilled in the art to practice same will be described in clear, concise and exact terms in conjunction with the accompanying drawings, wherein.

DESCRIPTION OF PREFERRED EMBODIMENTS OF INVENTION

Referring now more particularly to the drawings, like numerals in the various FIGS. will be employed to designate like parts.

Figure 1:
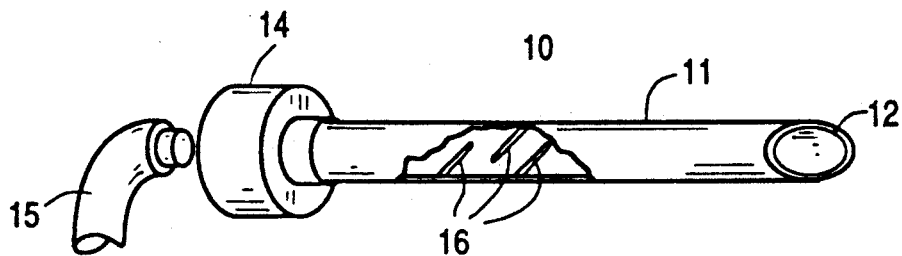
FIG. 1 is a perspective view of a nozzle suitable for use as a suction tip formed in accordance with the teachings of the invention, with parts broken away to reveal one suggested filter arrangement.

As illustratively shown in FIG. 1, the improved suction nozzle 10 is illustratively shown in a form suitable for use as a suction tip such as used by dentists. This nozzle 10 is as shown formed as conventionally of an elongate tube 11 of a generally circular cross-section, and provided with an entry tip 12 cut on a plane at a non-right angle with respect to the axis of the tube, so as to provide an entry opening of a cross-sectional area larger than the cross-sectional area of the tube. As is conventional, the end of the tube 11 remote from entry end 12 is formed with a connector 14 providing coupling means for joining the nozzle to the suction hose 15 of a suction system, which is illustratively shown in FIG. 1 as exploded away from the coupling 14.

Formed within the conventional nozzle structure 10 as above described, and as best seen in the cutaway portion illustrated in FIG. 1 are a plurality of spaced filtering projections 16. These filtering projections are arranged at an angle to the inner surface of the tube and extend opposite the direction of flow to impale any debris thereon. It is preferred that the projections extend along at least one third of the length of the tube, and that they extend from opposite sides of the tube. Each projection 16 is in the form of a pin or leaf-like member, and it is preferred that they be staggered both linearly and circumferentially about the inner tube wall.

Figure 2:
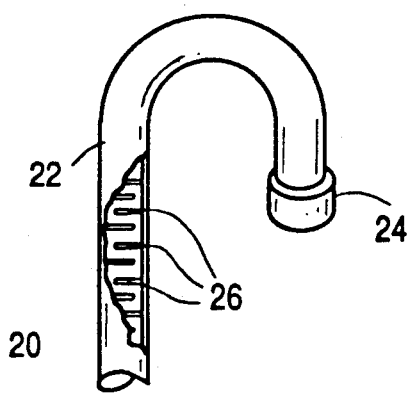
FIG. 2 is a perspective view with parts broken away of another embodiment of a disposable nozzle suitable for use as a saliva ejector with another form of filter.

In the embodiment of the invention illustrated in FIG. 2, the inventive concept is shown as embodied in connection with a saliva ejector 20 formed as conventionally of a flexible tube 22 which may be shaped to follow the contours accross the lip and into the mouth of a patient so as to permit positioning over the lower lip. This saliva ejector 20 is formed as conventionally with a rounded inlet tip 24 to minimize abrasion of any surrounding tissue contacted by the ejector. This protective inlet tip 24 is made perforate to permit uptake of fluid, and though the perforations provide some screening action, they are not sufficient to prevent the passage therethrough of debris. The debris passing into the saliva ejector will be stopped by the filtering means employed in this embodiment which is illustrated in the form of spaced staggered pin or leaf-like projection 26 extending perpendicularly from the side wall of the tube 22 into the tube. In this embodiment, the perpendicularly extending projections are preferably of a length such as to extend more than half way accross the interior of the tube 22 forming ejector 20. A connector (not shown) of the type illustrated by 14 in FIG. 1 is employed at the end of the saliva ejector 20 for connection to the suction line.

Figure 3:
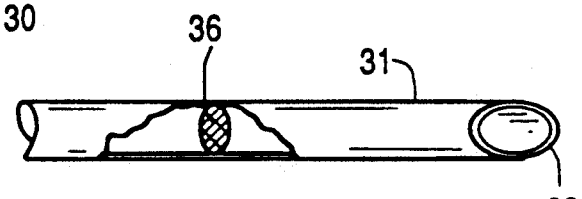
FIG. 3 is a perspective view of a suction tip with parts broken away to show a screen type filter.

In the embodiment of the invention illustrated in FIG. 3, a suction tip 30 of the type shown in FIG. 1 is employed formed of tube 31 having intake end 32 like end 12 in FIG. 1, and a connector such as 14 may be employed at the other end of tube 22. In this embodiment, instead of the projections 16 and 26 as illustrated in FIGS. 1 and 2 respectively, a grid or screen 36 is positioned extending in a plane across the flow path through tube 31.

Figure 4:
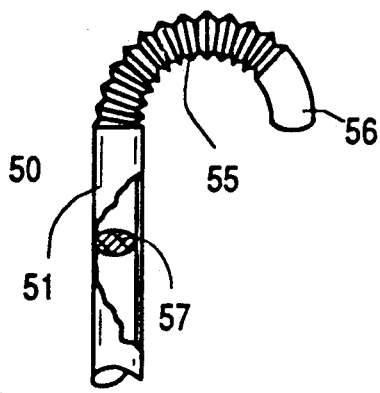
FIG. 4 is a perspective view of another form of nozzle provided with accordion folds along a length thereof to facilitate bending, and with parts broken away to show a filter in position.

In the FIG. 4 embodiment, the suction nozzle 50 is illustratively shown as formed for use as a saliva ejector. Suction nozzle 50 is formed of tube 51 provided with flexible accordion folds 55 along at least a part of or the entire length thereof. A tapered entry tip 56 is shown, and as understood, a connector such as 14 of FIG. 1 may be employed at the other end of tube 51. A screen filter 57 is positioned in the tube in a plane extending across the tube in a plane non-perpendicular with respect to the tube axis.

Figure 5:
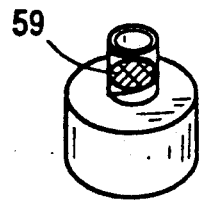
FIG. 5 is a perspective view of a nozzle connector with parts broken away to show another arrangement of the filter position.

In the FIG. 5 embodiment, instead of, or in addition to the placement of the filtering means 16, 26, 36 and 56 as shown in the FIG. 1, 2, 3 and 4 embodiments respectively, filtering means 59 are arranged in the connector 14, which as illustratively shown are of a grid screen type like screen filter 57.

Figure 6:
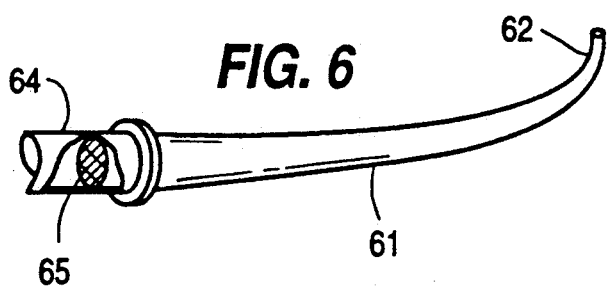
FIG. 6 is a perspective view of a high speed evacuation tip.

In the FIG. 6 embodiment, the nozzle 60 is of a high speed evacuation type formed with a tapered body 61 extending from a relatively small entry tip 62 to a connector end 64 adapted for coupling to a suction source. Arranged within the nozzle is a filter screen 65, as seen in the cut-away portion.

OPERATION

In use, as will be apparent to those skilled in the art, the suction nozzle, whether in the form of a surgical or dental high speed suction tip, as illustrated in FIGS. 1, 3 and 6, or a saliva ejector as in FIGS. 2 and 4, is formed of a relatively inexpensive fluid impervious material such as any one of a variety of plastics as currently employed in fabricating such tips. The suction tips are formed of tubing which is relatively rigid as compared to the flexible tubing employed in forming the saliva ejectors, all as conventional, and employing conventionally employed fabrication techniques. It is preferred that the material employed be biodegradable and contain both anti-coagulant and anti-microbial agents.

In the fabrication of these tips and the ejectors, in accordance with the teachings of the invention, filtering means are arranged within the tubing in the fluid flow path therethrough. As is apparent, though the particular means of fabrication form no part of this invention, it is contemplated that where filtering means are in the form of projections, as illustratively shown in FIGS. 1 and 2, conventional plastic molding techniques will be employed to form sheets with the desired projections thereon which are thereafter rolled into the desired tubing shapes. Where screen grid members such as 36, 57 and 65 are employed, these may obviously be fabricated separate and apart from the nozzles and inserted at some later date, or during fabrication of the nozzle. The tubing employed in forming the FIG. 4 nozzle will be provided with flexible accordion folds as illustrated. As understood by those skilled in the art, accordion folds may be employed in any nozzle, such for example as the nozzle types shown in FIGS. 1-6.

In accordance with the method of the invention, it is apparent that grids or other filtering members may readily be inserted into existing nozzles to provide desired filtering action in the nozzle removing substantially all of the debris before it enters the suction system.

After use of the nozzle or tip on each patient, proper usage would recommend discarding the nozzle with any debris entrained therein. As a result of the use of this filtering nozzle, the amounts of debris passing into the main suction sytem are significantly reduced, and the likelihood of patient infection from previously accumulated debris is minimized. Cycles of cleaning of the central suction sytem may be shortened, and the problems of cleaning reduced.

Where the nozzles are formed with accordion pleats as in FIG. 4, the use of these pleats permits bending of the tube without reduction of interior cross-section, thus offering minimal interference with flow through the tube. Additionally, the flexible accordion pleats may be selectively extended to permit extension of the nozle length. Further, the use of such pleats eliminates the need of a supporting wire as is required in conventional saliva ejectors.

The above disclosure has been given by way of illustration and elucidation and not by way of limitation, and it is desired to protect all embodiments of the herein disclosed inventive concept within the scope of the appended claims.

What is claimed is:

1. A disposable filtering suction nozzle comprising: an elongate tube having an entry end; filtering means formed of a plurality of spaced projections extending from the side walls of the tube into the interior of the tube into the fluid flow stream through said tube, said filtering means spaced from the entry end a distance such as not to interfere with the passage into the nozzle of any debris to be collected thereby in the flow path of any fluid passing through the nozzle; and coupling means formed integrally with the end of said tube opposite the entry end for connecting said tube to a suction source.

2. A filtering nozzle as in claim 1, in which said tube is of a flexible material subject to formation into a desired contour thereby adapted for use as a saliva ejector in dental procedures.

3. A filtering nozzle as in claim 1, in which said tube is formed of a relatively rigid material and formed with an intake orifice lying in a plane at a non-right angle to the axis of the tube.

4. A filtering suction nozzle as in claim 1, in which said projections comprise a series of pins extending at an angle to the axis of the tube.

5. Filtering suction nozzle as in claim 1, in which said projections comprise a plurality of perpendicularly extending members.

6. A filtering suction nozzle as in claim 1, in which said projections extend more than one half way across the interior of said tube.

7. A filtering suction nozzle as in claim 1, in which said filtering means are arranged in said coupling means.

8. A method of minimizing clogging of suction systems employed in dental and medical procedures wherein said suction systems utilize replaceable suction nozzles, said method comprising the steps of: arranging filtering means in the form of a plurality of spaced projections extending from the side walls of the nozzle into the fluid flow stream therethrough in the flow path of said suction nozzle within the nozzle to collect debris in the nozzle from the fluid passing therethrough.

* * * * *